(12) United States Patent
Lowe et al.

(10) Patent No.: US 7,220,701 B2
(45) Date of Patent: *May 22, 2007

(54) CATALYST AND PROCESS FOR SELECTIVE HYDROGENATION

(75) Inventors: David M. Lowe, Sunnyvale, CA (US); Michel Molinier, Houston, TX (US); John D. Y. Ou, Houston, TX (US); Michael A. Risch, Seabrook, TX (US); Anthony F. Volpe, Jr., Santa Clara, CA (US); Jeffrey C. Yoder, San Jose, CA (US)

(73) Assignee: ExxonMobil Chemical Patents Inc., Houston, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/720,617

(22) Filed: Nov. 24, 2003

(65) Prior Publication Data

US 2005/0113251 A1    May 26, 2005

(51) Int. Cl.
 *B01J 23/00* (2006.01)
 *B01J 23/48* (2006.01)
 *B01J 23/50* (2006.01)

(52) U.S. Cl. .................. 502/325; 502/347; 502/349

(58) Field of Classification Search ............... 502/325, 502/327, 349, 347
See application file for complete search history.

(56) References Cited

U.S. PATENT DOCUMENTS

| 3,651,167 | A |   | 3/1972  | Rosset |
|---|---|---|---|---|
| 3,793,232 | A |   | 2/1974  | Duhaut et al. |
| 3,859,377 | A |   | 1/1975  | Gross et al. |
| 4,149,961 | A |   | 4/1979  | Antos |
| 4,207,169 | A |   | 6/1980  | Courty et al. ............. 208/124 |
| 4,243,516 | A |   | 1/1981  | Martino et al. ............ 208/139 |
| 4,420,420 | A |   | 12/1983 | Mita et al. ................ 502/261 |
| 4,487,848 | A | * | 12/1984 | Robinson et al. .......... 502/223 |
| 4,522,935 | A | * | 6/1985  | Robinson et al. .......... 502/223 |
| 4,677,094 | A |   | 6/1987  | Moser et al. |
| 4,691,070 | A |   | 9/1987  | Nakamura et al. ......... 585/273 |
| 5,233,118 | A | * | 8/1993  | Bricker et al. ............. 585/660 |
| 5,356,851 | A |   | 10/1994 | Sarrazin et al. |
| 5,364,998 | A |   | 11/1994 | Sarrazin et al. ........... 585/259 |
| 5,536,695 | A | * | 7/1996  | Blejean et al. ............ 502/327 |
| 5,877,363 | A |   | 3/1999  | Gildert et al. ............ 585/260 |
| 5,965,481 | A |   | 10/1999 | Durand et al. |
| 6,084,140 | A |   | 7/2000  | Kitamura et al. |
| 6,096,933 | A |   | 8/2000  | Cheung et al. |
| 6,153,090 | A | * | 11/2000 | Le Peltier et al. ......... 208/137 |
| 6,187,985 | B1 | * | 2/2001  | Le Peltier et al. ......... 585/661 |
| 6,255,548 | B1 |   | 7/2001  | Didillon et al. ........... 585/259 |
| 6,355,854 | B1 |   | 3/2002  | Liu |
| 6,436,871 | B1 |   | 8/2002  | Liu |
| 6,498,280 | B1 |   | 12/2002 | Uzio et al. |
| 6,503,866 | B1 |   | 1/2003  | Shepherd et al. |
| 6,514,904 | B1 | * | 2/2003  | Moser et al. ............. 502/323 |
| 6,586,647 | B1 |   | 7/2003  | Abrevaya et al. |
| 6,777,371 | B2 |   | 8/2004  | Liu |
| 2002/0068843 | A1 |   | 6/2002 | Dai et al. ................ 585/260 |
| 2002/0136686 | A1 | * | 9/2002 | Takahashi ............... 423/651 |

FOREIGN PATENT DOCUMENTS

| WO | WO 98/47617 | 10/1998 |
|---|---|---|
| WO | WO 98/47618 | 10/1998 |
| WO | WO 98/47620 | 10/1998 |
| WO | WO 2004/046076 | 6/2004 |

OTHER PUBLICATIONS

Li, et al., "Selective Catalytic Reduction of NO Over Metal Oxide or Noble Metal-Doped $In_2O_3/Al_2O_3$ Catalysts By Propene in the Presence of Oxygen", Reaction Kinetics and Catalysis Letters, 2003, vol. 80, No. 1, pp. 75-80, XP008030692, no month.
H. Scott Fogler, Elements of Chemical Reaction Engineering, 2nd Edition, PTR Prentice Hall, Inc., pp. 29-52 (1992).
J. M. Smith, Chemical Engineering Kinetics, McGraw-Hill Book Company, pp. 231-279 (1956).
S. Asplund, "Coke Formation and Its Effect on Internal Mass Transfer and Selectivity in Pd-Catalysed Acetylene Hydrogenation", Journal of Catalysis, vol. 158, pp. 267-278 (1996).
U.S. Appl. No. 10/720,558, filed Nov. 24, 2003, Lowe et al.
U.S. Appl. No. 10/721,046, filed Nov. 24, 2003, Molinier et al.
U.S. Appl. No. 10/720,607, filed Nov. 24, 2003, Lowe et al.

* cited by examiner

*Primary Examiner*—J. A. Lorengo
*Assistant Examiner*—Patricia L. Hailey
(74) *Attorney, Agent, or Firm*—Andrew B. Griffis

(57) ABSTRACT

A selective hydrogenation catalyst composition comprises a rhodium component present in an amount such that the catalyst composition comprises less than 3.0% of rhodium by weight of the total catalyst composition; and an indium component present in an amount such that the catalyst composition comprises at least 0.3% and less than 5.0% of indium by weight of the total catalyst composition.

20 Claims, No Drawings

CATALYST AND PROCESS FOR SELECTIVE HYDROGENATION

CROSS REFERENCE TO RELATED APPLICATIONS

The present application is related by subject matter to U.S. patent application Ser. No. 10/720,558, filed Nov. 24, 2003 and U.S. Pat. application Ser. No. 10/720,607, filed Nov. 24, 2003 filed concurrently herewith, the entire contents of which applications are incorporated herein by reference.

FIELD

This invention relates to a catalyst and a process for the selective hydrogenation of alkynes and diolefins to olefins.

BACKGROUND

Light olefins, such as ethylene, propylene and butylenes, can be produced using various processes such as steam cracking, fluid catalytic cracking, conversion of methanol to olefins, paraffin dehydrogenation, alcohol dehydration, methane coupling and Fischer Tropsch reactions. However, these processes often produce varying levels of acetylenic or diene by-products, such as acetylene, methyl acetylene (MA), propadiene (PD), butyne and butadiene. These by-products must be removed from the light olefin streams because they can act as poisons to the downstream processing catalysts, such as polymerization catalysts. The preferred method of removing these by-products is by selective hydrogenation in which, for example, the acetylenes are converted to ethylene, methyl acetylene and propadiene are converted to propylene, and the butyne and butadiene are converted to butylenes.

Currently, the commercial catalysts used for this selective hydrogenation comprise nickel or palladium, such as palladium and silver, on an alumina support. However, in addition to producing the desired olefin products, these catalysts tend to generate significant quantities of saturates (for example, ethane, propane and butanes) as a result of over-hydrogenation and green oil (olefin oligomers) as a result of competing oligomerization reactions. Both of these by-products are undesirable in that they reduce the selectivity to the required light olefins. However, the green oil is particularly problematic in that it decreases the life of the hydrogenation catalyst.

There is therefore a need for an improved catalyst for the selective hydrogenation of alkynes and diolefins, wherein the catalyst exhibits increased olefin selectivity and reduced selectivity to saturates and oligomers, such as green oil, while retaining high hydrogenation activity.

U.S patent application Publication No. 2002/0068843 discloses a catalyst for selectively hydrogenating acetylenic and diolefinic compounds with low green oil formation, the catalyst comprising the following active components loaded on a porous inorganic support: (1) at least one of platinum, palladium, nickel, ruthenium, cobalt, and rhodium; (2) at least one of silver, copper, zinc, potassium, sodium, magnesium, calcium, beryllium, tin, lead, strontium, barium, radium, iron, manganese, zirconium, molybdenum, and germanium; (3) at least one rare earth metal selected from scandium, yttrium and Lanthanides in Group IIIB of Periodic Table of Elements; and (4) bismuth. Preferably, component (1) is platinum or palladium component (2) is silver, potassium or sodium and component (3) is lanthanum or neodymium.

U.S. Pat. No. 6,255,548 discloses a method for selectively hydrogenating a feed comprising an acetylenic compound and/or a diolefin in the presence of a catalyst comprising at least one support, at least one Group VIII metal selected from nickel, palladium, platinum, rhodium, ruthenium and iridium and at least one additional element M selected from germanium, tin, lead, rhenium, gallium, indium, thallium, gold, and silver, wherein the catalyst is formed by introducing said additional element M into an aqueous solvent in the form of at least one water-soluble organometallic compound comprising at least one carbon-M bond. The preferred Group VIII metals are nickel, palladium and platinum and the preferred additional elements M are germanium, tin, gold, and silver. There is no specific disclosure of a catalyst comprising rhodium and indium and no indication is given as to the molar ratio of the Group VIII metal to the additional element M, especially if the Group VIII metal is rhodium and/or M is indium.

U.S. Pat. No. 5,877,363 discloses a process for the removal of acetylenes and 1,2-butadiene from a $C_4$ aliphatic hydrocarbon stream by contacting the hydrocarbon stream with hydrogen in a distillation column reactor containing a bed of hydrogenation catalyst comprising a GroupVIII metal selected from platinum, palladium, rhodium or mixtures thereof; optionally in combination with a Group IB or Group VIB metal, and fractionally distilling the reaction mixture to remove a heavier fraction and removing a fraction overhead comprising substantially all of the $C_4$ compounds having reduced acetylenes and 1,2-butadiene content. The preferred hydrogenation catalyst is palladium.

U.S. Pat. Nos. 5,356,851 and 5,364,998 disclose a catalyst and a process for the selective hydrogenation of unsaturated compounds, wherein the catalyst contains 0.1 to 10%, preferably 0.2 to 5%, of at least one Group VIII metal selected from nickel, palladium, platinum, rhodium and ruthenium and 0.01 to 10%, preferably 0.1 to 5%, of at least one Group IIIA metal selected from gallium and indium. The molar ratio of Group IIIA metal to Group VIII metal is between 0.2 and 5, preferably between 0.3 and 2. The metals are deposited on a catalyst support, such as silica, alumina or silica-alumina, by (a) impregnating the support with a solution of a Group IIIA metal compound precursor, then (b) impregnating the product of (a) with a solution of a Group VIII metal compound and then (c) calcining the product of (b) at 110 to 600° C. The preferred Group VIII metals are nickel, palladium and platinum. There is no specific disclosure of a catalyst comprising rhodium and indium.

In U.S. Pat. No. 4,691,070 a catalyst for the hydrogenation of a diolefin is disclosed in which palladium or a compound thereof and at least one co-catalyst component selected from ruthenium, rhodium, cobalt, and rhenium are supported each in the form of an elemental metal or a metal compound on a non-acidic support.

A rhodium catalyst is disclosed in U.S. Pat. No. 4,420,420 in which active rhodium metal is supported on a silica type or titania type support, optionally together with one or more co-catalysts including alkaline earth metals, such as calcium, magnesium, barium and the like, noble metals, such as platinum, palladium, iridium, ruthenium, gold and the like, iron, nickel, cobalt, cerium and manganese.

SUMMARY

In one aspect, the present invention resides in a catalyst composition comprising:
- (a) a rhodium component present in an amount such that the catalyst composition comprises less than 3.0% of rhodium by weight of the total catalyst composition; and
- (b) an indium component present in an amount such that the catalyst composition comprises at least 0.3% and less than 5.0% of indium by weight of the total catalyst composition.

In one embodiment, the catalyst composition comprises at least 0.25% and less than 2.5%, for example at least 0.3% and less than 1.5%, of rhodium by weight of the total catalyst composition. In addition, the catalyst composition comprises at least 0.4% and less than 4.0%, such as at least 0.5% and less than 3%, of indium by weight of the total catalyst composition.

Conveniently, the molar ratio of the rhodium to indium in the catalyst composition is about 0.2 to about 1.1, such as from about 0.35 to about 0.75.

Conveniently, the catalyst composition also comprises a support.

In a further aspect, the invention resides in a method for making a catalyst composition, the method comprising:
- (a) applying a rhodium compound to a support; and
- (b) applying an indium compound to the support;

to produce a catalyst composition which comprises less than 3.0% rhodium and at least 0.3% and less than 5.0% of indium by weight of the total catalyst composition including the support.

Conveniently, after at least one of (a) and (b), the support is calcined at a temperature of about 100° C. to about 600° C.

In yet a further aspect, the invention resides in use of the catalyst composition described above in a process for selectively removing alkynes or diolefins, particularly alkynes or diolefins having 2 to 4 carbon atoms, from a feedstock containing olefins, particularly $C_2$ to $C_4$ olefins.

DETAILED DESCRIPTION OF THE EMBODIMENTS

The present invention relates to a novel catalyst composition, its preparation and its use in the hydrogenation of alkynes or diolefins or both in a feedstock containing other unsaturated compounds, such as olefins. The catalyst comprises indium and rhodium within particular weight ranges and is capable of hydrogenating any alkynes and diolefins in the feedstock with high selectivity to olefins and low selectivity to green oil (oligomers) and saturates. A further benefit of the present catalyst composition is the extension of catalyst lifetime and/or operating cycle due to the reduction in green oil formation. In addition, the catalyst of the invention has improved tolerance to carbon monoxide impurities in the feedstocks and can, for example, be employed with feedstocks containing carbon monoxide in amounts up to 1 ppm, such as up to 0.5 ppm, for example up to 0.1 ppm.

As used herein, the term "acetylene" includes the hydrocarbon $C_2H_2$ as well as other acetylenic hydrocarbons, such as methyl acetylene (MA). The term "ethylene product stream" includes streams containing the hydrocarbon $C_2H_4$ as well as streams containing other mono- and diolefinically unsaturated hydrocarbons. It will be appreciated, however, that while the catalysts are often discussed in terms of selectively hydrogenating acetylene, MA, propadiene (PD) and optionally, butadiene (BD) in a stream that is predominantly ethylene, propylene and/or butylenes, they are not necessarily limited to the treatment of streams that contain ethylene or propylene or butene, but are expected to find applicability to the selective hydrogenation of other unsaturated compounds in streams of other chemical content as well.

Catalyst Composition

The present catalyst composition comprises rhodium and indium as active components, which may be combined with a support. In general, the rhodium and indium components will be present in the catalyst composition in elemental form, but one or both of these components may also be present at least partly in other forms, such as oxide, hydride or sulfide forms.

In particular, the catalyst composition includes a rhodium component which is present in the catalyst composition in an amount such that the catalyst composition comprises less than 3.0%, for example at least 0.25% and less than 2.5%, such as at least 0.3% and less than 1.5%, of rhodium by weight of the total catalyst composition.

In addition, the catalyst composition includes an indium component which is present in the catalyst composition in an amount such that the catalyst composition comprises at least 0.3% and less than 5.0%, for example at least 0.4% and less than 4.0%, such as at least 0.5% and less than 3%, of indium by weight of the total catalyst composition.

All weight percentages for the metal components of the catalyst composition are based on the amount of elemental metal present by weight of the total catalyst composition, including any binder or support.

Other catalytically active metal components may also be present in the catalyst composition but, provided the indium and rhodium are present in the amounts discussed above, the present catalyst composition is found to exhibit improved performance in the selective hydrogenation of alkynes and diolefins without the need for additional catalytically active metals.

In addition to the active metal components discussed above, the catalyst composition may comprise a support or binder material. Suitable support materials comprise carbon, silicon carbide, silicon nitride, boron nitride, magnesium silicate, bentonite, zeolites, metal alloys, zirconia, alumina, silica, silica-alumina, ceria-alumina, aluminates (such as aluminates of Groups 1 and 2 and of the Periodic Table of Elements) and magnesium oxide-silicon oxide mixtures. Preferred support materials include zirconia, alumina and ceria-alumina. The binder or support material conveniently comprises from about 75 wt % to about 99.9 wt %, such as from about 92.5 wt % to about 99.5 wt %, of the entire catalyst composition.

The active metal components may be substantially uniformly distributed throughout the support, can be located within a thin layer at the support surface (commonly referred to as eggshell), can be located at the center of the support (commonly referred to as eggyolk), or can be concentrated between the outer edge and the center of the support (commonly referred to as eggwhite). Preferably, the metal components are concentrated in a thin layer (not more than 1000 microns, conveniently not more than 500 microns, such as not more than 300 microns, for example not more than 100 microns deep) on the surface of the support.

Method of Making the Catalyst Composition

The catalyst composition can be prepared by a variety of different procedures. One suitable procedure is impregnation in which a support, such as alumina, is contacted with an aqueous or organic solution of a compound (such as a nitrate, sulfate, halide or acetate) of the chosen metal or metals (rhodium and/or indium), the solution volume being about equal to or in excess of the retention volume of the support. Contact between the support and the solution is normally maintained for about 0.01 to about 24 hours, such as about 0.05 to about 4 hours, whereafter the impregnated support is dried and normally calcined. Such a procedure can be used to add rhodium and indium to the support in a single operation or alternatively separate impregnations can be used to apply rhodium and indium successively to the support.

Alternatively, at least one of the metal components can be applied to the support by mixing a slurry or solution of a compound of the chosen metal or metals with a slurry of a particulate support in a liquid, such as water. After mixing, the resultant slurry may be treated, such as by heating or vacuum drying, to partially or completely remove the liquid, whereafter the treated support may, if necessary, be filtered, then washed with distilled water, dried and calcined as in the case of the impregnation procedure.

As a further alternative, at least one of the metal components can be applied to the support by precipitation. For example, a liquid solution, such as an aqueous solution, comprising a source of ions of one of the active components can be subjected to conditions sufficient to cause precipitation of the component as a solid from solution, such as by the addition of a precipitating reagent to the solution. Conveniently, the precipitation is conducted at a pH above 7. For example, the precipitating agent may be a base such as sodium hydroxide or ammonium hydroxide.

In addition, both of the rhodium and indium components can be applied to the support simultaneously by co-precipitation. For example, a first liquid solution comprising a source of rhodium ions can be combined with a second liquid solution comprising a source of indium ions. This combination of two solutions can take place under conditions sufficient to cause co-precipitation of both components onto the support from the liquid medium. Alternatively, the source of rhodium ions and the source of indium ions may be combined into a single solution. This solution may then be subjected to conditions sufficient to cause co-precipitation of the solid components onto the support, such as by the addition of a precipitating reagent to the solution.

Although any compound of the desired metal can be used to apply the different catalyst components to the support, it is found that in the case of rhodium, the preferred compound used to apply the rhodium to the support is rhodium nitrate, whereas in the case of indium, the preferred compounds are indium nitrate and indium formate.

After applying the metal components to the support, the support is normally calcined, such as in air, at between about 100° C. and about 600° C., for example at between about 110° C. and about 500° C. Where the metal components are applied to the support in consecutive steps, a separate calcination step can be conducted after each metal application step or a single calcination step can be conducted after all the metal components have been applied to the support.

Finally, the catalyst composition is conveniently heated in a reducing atmosphere, such as an atmosphere containing about 5 to about 30 mol % hydrogen, with the remainder being an inert gas, such as nitrogen, at a temperature of about 100° C. to about 600° C., such as about 300° C. to about 500° C., to further increase the activity of the catalyst. Such a reduction step can be performed in addition to, or in place of, the calcination step(s) referred to above.

Selective Hydrogenation Process

The catalyst composition of the invention is capable of hydrogenating alkynes and diolefins in a feedstock that also contains olefins with high selectivity to olefins and low selectivity to green oil (olefin oligomers) and saturates. In particular, when used to selectively hydrogenate $C_2$ to $C_4$ alkynes and/or diolefins in a feedstock also containing $C_2$ to $C_4$ olefins, the present catalyst composition typically achieves an alkyne conversion in excess of 80%, such as in excess of 90%, with an olefin selectivity in excess of 45%, such as in excess of 70%, by weight of the total product and a green oil selectivity of less than 20%, for example less than 15%, such as less than 10%, by weight of the total product. The reduction in green oil formation should also result in an extension of catalyst lifetime and/or operating cycle.

The selective hydrogenation of acetylene, methyl acetylene (MA), propadiene (PD), and/or butadiene (BD) is typically carried out in one of four unit types:

(a) Front-End Selective Catalytic Hydrogenation Reactors, where the feed is composed of $C_3$ and lighter hydrocarbons, or $C_2$ and lighter hydrocarbons. In the case of raw gas applications, other components such as butadiene, ethyl acetylene, dimethyl acetylene, vinyl acetylene, cyclopentadiene, benzene, and toluene can also be present.

(b) Back-End Selective Catalytic Hydrogenation Reactors, where the feed is composed of an ethylene-rich stream.

(c) MAPD Selective Catalytic Hydrogenation Reactors, where the feed is composed of a propylene-rich stream.

(d) BD Selective Catalytic Hydrogenation Reactors, where the feed is composed of a butylene-rich stream.

The operating parameters of an alkyne/alkadiene selective hydrogenation process are not narrowly critical and can be controlled in view of a number of interrelated factors including, but not necessarily limited to, the chemical composition of the feedstock, the control systems and design of a particular plant, etc. (i.e., different reactor configurations including front-end, back-end, MAPD, and BD converters as mentioned briefly above). In general, however, suitable operating parameters include a temperature of from about 20° C. to about 150° C., such as from about 30° C. to about 100° C., a pressure of from about 100 psig to about 580 psig (690 kPa to 4100 kPa), such as from about 200 psig to about 440 psig (1400 kPa to 3400 kPa), a $H_2/C_2H_2$ molar feed ratio of from about 1 to about 1000, such as from about 1.1 to about 800 and, assuming the reaction is in the vapor phase, a GHSV from about 100 to about 20,000, such as from about 500 to about 15,000 or, if the reaction is in the liquid phase, an LHSV of 0.1 to 100, such as from 1 to 25.

The following descriptions serve to give some sense of how the inventive process may be practiced in the different commercial units.

In the case of a front-end (FE) selective hydrogenation reactor, the inlet operating temperature may range from about 30 to about 150° C., such as from about 50 to about 100° C. Representative operating pressures may range from about 100 psig to about 500 psig (about 690 to 3,500 kPa), such as from about 200 psig to about 400 psig (about 1400 to 2800 kPa). The GHSV may range from about 5000 to about 20,000, such as from about 8000 to about 15,000. Further, the $H_2$ partial pressure may range from about 25 psig to about 175 psig (about 172 to 1200 kPa), such as from about 50 psig to about 140 psig (about 345 to 965 kPa). The feedstreams in FE selective hydrogenation processes typically contain at least about 20% ethylene, and less than 1% acetylene, with the balance comprising ethane, methane, (All percentages are mole% unless otherwise noted).

Depending upon the process configuration of the plant, this feed stream can also contain $C_3$ components such as methyl acetylene, propadiene, propylene, and propane. Still heavier components such as 1,3 butadiene; 1,2 butadiene; ethyl acetylene; dimethyl acetylene; vinyl acetylene; cyclopentadiene; benzene; toluene and mixtures thereof may also be present as a result of certain process configurations.

In the case of a back-end selective hydrogenation reactor, the inlet operating temperature may range from about 30 to about 150° C., such as from about 40 to about 90° C. Representative operating pressures may range from about 100 psig to about 500 psig (about 690 to 3,500 kPa), such as from about 200 psig to about 400 psig (about 1400 to 2800 kPa). The GHSV may range from about 1000 to about 10,000, such as from about 3000 to about 8000. Further, the $H_2/C_2H_2$ molar feed ratio may range from about 0.5 to about 20, such as from about 1.0 to about 1.5. The feedstreams in back-end selective hydrogenation processes may contain about 2% acetylene, about 70% ethylene, and the balance of other $C_2$ compounds.

In the case of a methyl acetylene/propadiene (MAPD) selective hydrogenation reactor, operation can be conducted in either the liquid or vapor phase. In the case of liquid phase operation, the inlet operating temperature may range from about 20 to about 100° C., such as from about 30 to about 80° C. Representative operating pressures may range from about 150 psig to about 600 psig (about 1000 to 4100 kPa), such as from about 250 psig to about 500 psig (about 1700 to 3400 kPa). The LHSV may range from about 0.1 to about 100, such as from about 1 to about 10. In the case of the vapor phase operation, the inlet operating temperature may range from about 20 to about 600° C., such as from about 200 to about 400° C. Representative operating pressures may range from about 150 psig to about 600 psig (about 1000 to 4100 kPa), such as from about 250 psig to about 500 psig (about 1700 to 3400 kPa). The GHSV may range from about 100 to about 20,000, such as from about 500 to about 5000. Further, the $H_2/C_2H_2$ molar feed ratio may range from about 0.5 to about 20, such as from about 1 to about 10. The feedstreams in MAPD selective hydrogenation processes may contain at least 80% propylene, and less than 10% of a compound selected from the group consisting of methyl acetylene, propadiene, and mixtures thereof.

In the case of a butadiene (BD) selective hydrogenation reactor, operation can be conducted in either the liquid or vapor phase. In the case of liquid phase operation, the inlet operating temperature may range from about 20 to about 120° C., such as from about 40 to about 100° C. Representative operating pressures may range from about 150 psig to about 600 psig (about 1000 to 4100 kPa), such as from about 200 psig to about 400 psig (about 1400 to 2800 kPa). The LHSV may range from about 0.1 to about 100, such as from about 1 to about 25. In the case of the vapor phase operation, the inlet operating temperature may range from about 20 to about 600° C., such as from about 50 to about 200° C. Representative operating pressures may range from about 150 psig to about 600 psig (about 1000 to 4100 kPa), such as from about 250 psig to about 500 psig (about 1700 to 3400 kPa). The GHSV may range from about 100 to about 20,000, such as from about 500 to about 5000. Further, the $H_2/C_2H_2$ molar feed ratio may range from about 0.5 to about 20, preferably from about 1 to about 10. The feedstreams in BD selective hydrogenation processes may contain at least 90% butylene, and greater than 0.2% butadiene.

The invention will now be more particularly described with reference to the following Examples.

In the Examples, the following definitions are employed:

$$C_2H_2 \text{ Conversion:} \quad \frac{(C_2H_2)_{in} - (C_2H_2)_{out}}{(C_2H_2)_{in}} \times 100$$

$$C_2H_4 \text{ (Gain) Selectivity:} \quad \frac{(C_2H_2)_{in} - (C_2H_2)_{out} - C_2H_{6\,produced} - (2XC_{4\,produced} + 3XC_{6\,produced})}{(C_2H_2)_{in} - (C_2H_2)_{out}} \times 100$$

$$C_2H_6 \text{ Selectivity:} \quad \frac{C_2H_{6\,produced}}{(C_2H_2)_{in} - (C_2H_2)_{out}} \times 100$$

$$\text{Green-Oil Selectivity:} \quad \frac{(2XC_{4\,produced}) + (3XC_{6\,produced})}{(C_2H_2)_{in} - (C_2H_2)_{out}} \times 100$$

EXAMPLE 1 (COMPARATIVE)

This example illustrates the performance of a current state of the art commercial Pd-based catalyst. The catalyst, G-58C, was obtained from Sud-Chemie, Inc. and comprised 0.03 wt % Pd and 0.18 wt % Ag on alumina. The catalyst was evaluated under the following conditions: temperature=100° C., pressure=300 psig, GHSV=4500, $H_2/_2H_2$ feed ratio=1.1. The hydrocarbon feed contained nominally 1.65 mole % acetylene and 70 mole % ethylene, with balance being nitrogen. Impurities that may be present in the feed include carbon monoxide (<0.5 ppm), mercury, arsine, phosphorus (<5 ppb), sulfur (<1 ppm), oxygen (<1 ppm), water (<10 ppm), acetone (<10 ppm) and methanol (<2 ppm). Test results are given in Table 1 below.

TABLE 1

| Catalyst | $C_2H_2$ conv (%) | $H_2$ conv (%) | $C_2H_4$ select (%) | $C_2H_6$ select (%) | Green Oil select (%) |
|---|---|---|---|---|---|
| G58-C | 84.8 | 100 | 60.1 | 15.3 | 24.6 |

EXAMPLE 2

10 g of theta-alumina (SBa-90 supplied by Sasol) were mixed with 50 ml of deionized water and a slurry was obtained. Then 0.1 89 gm $Rh(NO_3)_3 \cdot 2H_2O$ was dissolved in 80 ml deionized water and was mixed with 0.314 g In $(NO_3)_3 \cdot xH_2O$ dissolved in 50 ml deionized water. The solution containing both metals was added to the alumina slurry and, after 1 hour stirring, the slurry was gently heated until most of the water was removed. The resulting paste was dried in a vacuum oven for 2 hours at 100° C., whereafter the remaining powder was calcined in air for 2 hours at 120° C. and then for 4 hours at 450° C. The resultant catalyst composition was then reduced at 350° C. for 5 hours in a helium atmosphere containing 5 mol % hydrogen.

The final catalyst contained 0.6 wt % rhodium and 1.2 wt % indium and had a rhodium to indium molar ratio of 0.5. When the catalyst was used to treat the same hydrocarbon feed under the same conditions as Example 1, the results summarized in Table 2 were obtained.

TABLE 2

| Catalyst | C$_2$H$_2$ conv (%) | H$_2$ conv (%) | C$_2$H$_4$ select (%) | C$_2$H$_6$ select (%) | Green Oil select (%) |
|---|---|---|---|---|---|
| 0.6 wt % Rh/ 1.2 wt % In | 79.5 | 100 | 55.9 | 37.1 | 7 |

It will be seen that, although the acetylene conversion and ethylene selectivity in Examples 1 and 2 were very similar, the catalyst of Example 2 reduced the production of green oil by a factor of about 3.5.

EXAMPLES 3 TO 5

The process of Example 2 was repeated with varying amounts of the rhodium and indium precursors and with the reduction temperature increased to 450° C. to prepare three additional Rh/In catalysts having the following compositions:
Example 3=0.6 wt % Rh and 1.2 wt % In,
Example 4=1.2 wt % Rh and 2.4 wt % In,
Example 5=2.4 wt % Rh and 4.8 wt % In.
When the catalysts were used to treat the same hydrocarbon feed under the same conditions as Example 1, the results shown in Table 3 were obtained.

TABLE 3

| Example | C$_2$H$_2$ conv (%) | H$_2$ conv (%) | C$_2$H$_4$ select (%) | C$_2$H$_6$ select (%) | Green Oil select (%) |
|---|---|---|---|---|---|
| 3 | 93.4 | 100 | 64.3 | 29.7 | 6.1 |
| 4 | 81.0 | 100 | 45.2 | 48.2 | 6.6 |
| 5 | 73.3 | 100 | 30.7 | 62.9 | 6.4 |

It will be seen from Table 3 that, as the rhodium content increased from 0.6 wt % to 2.4 wt % and the indium content increased from 1.2 wt % to 4.8 wt %, the acetylene conversion and the ethylene selectivity decreased rapidly.

EXAMPLES 6 TO 22

A series of catalysts each containing 0.6 wt % indium and 1.2 wt % rhodium were prepared using different rhodium and indium precursor salts and different supports. In each case, a mixed solution containing both rhodium and indium ions was prepared and was used to impregnate the support using an incipient wetness technique. The impregnation was conducted agitating the support with the mixed indium-rhodium solution in a vial by vibration for 30 minutes at room temperature (25° C.). After impregnation, the support was dried at 120° C. for 3 hours and then calcined in air at 450° C. for 4 hours. The calcined catalyst was then subjected to reduction in a stream of 5% H$_2$ in N$_2$ at 450° C. for 5 hours.

When sulfate precursor salts were employed, the rhodium component was obtained by diluting rhodium (III) sulfate (Aldrich, 8 wt % rhodium) with deionized water to 2.48 wt % rhodium, whereas the indium component was obtained by adding solid indium sulfate (Aldrich, 2.15 g) to 6.49 g deionized water and 0.46 g concentrated sulfuric acid to afford an 8.13 wt % indium solution. When nitrate precursor salts were employed, the rhodium component was obtained by diluting rhodium nitrate (Strem chemicals, 10.01 wt % solution) with deionized water to 3.51 wt % rhodium, whereas the indium component was obtained by dissolving solid indium nitrate trihydrate (Prochem) in sufficient deionized water to give a solution containing 8.13 wt % indium. When chloride precursor salts were employed, the rhodium component was obtained by dissolving solid rhodium chloride hydrate (Alfa, 1.0953 g) in 20.42 g deionized water to afford a 2.50 wt % rhodium solution, whereas the indium component was obtained by dissolving solid indium chloride tetrahydrate (Aldrich, 4.37 g) in 12.57 g deionized water to afford a 9.98 wt % indium solution.

Details of the impregnations are set out below.

In Example 6, the support was Norton SA6175 alumina which had been heat treated at 975° C. for 15 minutes to convert gamma phase to theta phase. The prepared rhodium sulfate solution (167.3 μL) and indium sulfate solution (89.5 μL) were mixed with deionized water (343.2 μL) and this mixed rhodium-indium solution (120 μL) was added to 148 mg of the alumina in a vial.

In Example 7, the alumina of Example 6 was used as the support and a rhodium-indium solution (120 μL) obtained by mixing the prepared rhodium nitrate solution (121.6 μL) and indium nitrate solution (62.3 μL) with deionized water (416.1 μL) was added to 148 mg of the alumina in a vial.

In Example 8, the support was Aerolyst 350 silica supplied by Degussa and was used as received. The prepared rhodium chloride solution (125.8 μL) and indium chloride solution (55.0 μL) were mixed with deionized water (314.1 μL) and this mixed rhodium-indium solution (99 μL) was added to 108 mg of the silica in a vial.

In Example 9, the silica of Example 8 was used as the support and a rhodium-indium solution (99 μL) obtained by mixing the prepared rhodium sulfate solution (122.1 μL) and indium sulfate solution (65.3 μL) with deionized water (307.8 μL) was added to 108 mg of the silica in a vial.

In Example 10, the silica of Example 8 was again used as the support and a rhodium-indium solution (99 μL) obtained by mixing the prepared rhodium nitrate solution (88.8 μL) and indium nitrate solution (45.5 μL) with deionized water (360.8 μL) was added to 108 mg of the silica in a vial.

In Example 11, the support was Norton XZ16052 zirconia and was used as received. The prepared rhodium chloride solution (365.8 μL) and indium chloride solution (160.0 μL) were mixed with deionized water (74.2 μL) and this mixed rhodium-indium solution (120 μL) was added to 314 mg of the zirconia in a vial.

In Example 12, the zirconia of Example 11 was used as the support and a rhodium-indium solution (120 μL) obtained by mixing the prepared rhodium sulfate solution (355.0 μL) and indium sulfate solution (189.9 μL) with deionized water (55.1 μL) was added to 314 mg of the zirconia in a vial.

In Example 13, the zirconia of Example 11 was again used as the support and a rhodium-indium solution (120 μL) obtained by mixing the prepared rhodium nitrate solution (355.0 μL) and indium nitrate solution (189.9 μL) with deionized water (55.1 μL) was added to 314 mg of the zirconia in a vial.

In Example 14, the support was Aerolyst 7708 titania supplied by Degussa and was used as received. The prepared rhodium chloride solution (268.0 μL) and indium chloride solution (117.2 μL) were mixed with deionized water (17.4 μL) and this mixed rhodium-indium solution (80 μL) was added to 230 mg of the titania in a vial.

In Example 15, the titania of Example 14 was used as the support and a rhodium-indium solution (80 μL) obtained by mixing the prepared rhodium sulfate solution (260.0 μL) and indium sulfate solution (139.1 µL) with deionized water (3.34 µL) was added to 230 mg of the titania in a vial.

In Example 16, the titania of Example 14 was again used as the support and a rhodium-indium solution (80 µL) obtained by mixing the prepared rhodium nitrate solution (189.0 µL) and indium nitrate solution (96.8 µL) with deionized water (116.7 µL) was added to 230 mg of the titania in a vial.

In Example 17, the support was zirconia-silica (MA1030Zr1) supplied by PQ Corporation and was used as received. The prepared rhodium chloride solution (107.2 µL) and indium chloride solution (46.9 µL) were mixed with deionized water (407.2 µL) and this mixed rhodium-indium solution (112 µL) was added to 92 mg of zirconia-silica in a vial.

In Example 18, the zirconia-silica of Example 17 was used as the support and a rhodium-indium solution (112 µL) obtained by mixing the prepared rhodium sulfate solution (104.0 µL) and indium sulfate solution (55.7 µL) with deionized water (401.6 µL) was added to 92 mg of zirconia-silica in a vial.

In Example 19, the zirconia-silica of Example 17 was again used as the support and a rhodium-indium solution (112 µL) obtained by mixing the prepared rhodium nitrate solution (75.6 µL) and indium nitrate solution (38.7 µL) with deionized water (446.9 µL) was added to 92 mg of zirconia-silica in a vial.

In Example 20, the support was titania-silica supplied by PQ Corporation and was used as received. The prepared rhodium chloride solution (122.3 µL) and indium chloride solution (53.2 µL) were mixed with deionized water (344.2 µL) and this mixed rhodium-indium solution (104 µL) was added to 105 mg of titania-silica in a vial.

In Example 21, the titania-silica of Example 20 was used as the support and a rhodium-indium solution (104 µL) obtained by mixing the prepared rhodium sulfate solution (118.7 µL) and indium sulfate solution (63.5 µL) with deionized water (337.8 µL) was added to 105 mg of titania-silica in a vial.

In Example 22, the titania-silica of Example 20 was used as the support and a rhodium-indium solution (104 µL) obtained by mixing the prepared rhodium sulfate solution (118.7 µL) and indium sulfate solution (63.5 µL) with deionized water (337.8 µL) was added to 105 mg of titania-silica in a vial.

When the resultant catalysts were used to treat the same hydrocarbon feed under the same conditions as Example 1, the results shown in Table 4 were obtained.

The results in Table 4 show that nitrate precursors consistently produce significantly better catalysts than chloride and sulfate precursors and that alumina and zirconia are superior supports to silica, titania, silica-zirconia and titania-silica supports. The negative values in Table 4 are the result of the equations referred to above and used to calculate conversion and selectivity. Thus it will be appreciated that experimental error in measuring species concentrations can lead to the calculation of negative values in the above equations when conversions are extremely low.

TABLE 4

| Example | Precursors | Support | $C_2H_2$ conv (%) | $H_2$ conv (%) | $C_2H_4$ select (%) | $C_2H_6$ select (%) | Green Oil select (%) |
|---|---|---|---|---|---|---|---|
| 6 | Sulfates | Alumina | 26.3 | 34.9 | 20.3 | 62.0 | 17.7 |
| 7 | Nitrates | Alumina | 83.8 | 93.4 | 59.7 | 34.7 | 5.7 |
| 8 | Chlorides | Silica | 0.8 | 1.0 | 29.6 | 64.4 | 6.0 |
| 9 | Sulfates | Silica | −0.7 | −0.1 | 129.8 | −29.8 | 6.0 |
| 10 | Nitrates | Silica | −0.7 | 1.9 | 150 | −50 | −21.2 |
| 11 | Chlorides | Zirconia | 46.3 | 63.0 | 21.9 | 63.9 | 14.2 |
| 12 | Sulfates | Zirconia | 8.2 | 12.0 | −17.5 | 90.7 | 26.7 |
| 13 | Nitrates | Zirconia | 51.4 | 76.8 | 7.8 | 79.2 | 13.1 |
| 14 | Chlorides | Titania | 7.5 | 8.7 | 35.5 | 47.0 | 17.5 |
| 15 | Sulfates | Titania | 8.0 | 10.9 | 20.2 | 66.2 | 13.6 |
| 16 | Nitrates | Titania | 20.0 | 23.5 | 50.6 | 40.8 | 8.5 |
| 17 | Chlorides | Zirconia-Silica | 0.8 | 1.1 | 55.6 | 44.4 | 0 |
| 18 | Sulfates | Zirconia-Silica | 0.3 | 0.9 | −50.0 | 150.0 | 18.0 |
| 19 | Nitrates | Zirconia-Silica | 1.5 | 2.2 | 63.6 | 33.1 | 3.3 |
| 20 | Chlorides | Titania-Silica | 0.9 | 1.4 | 28.8 | 64.2 | 7.0 |
| 21 | Sulfates | Titania-Silica | 0.3 | 2.4 | −50 | 150.0 | 27.1 |
| 22 | Nitrates | Titania-Silica | −0.3 | 2.4 | 150 | −50.0 | −50.0 |

EXAMPLES 23 TO 28

A series of catalysts each containing 0.6 wt % indium and 1.2 wt % rhodium were prepared using different rhodium and indium precursor salts and a ceria/alumina support (Norpro, 50% $CeO_2/Al_2O_3$, 135 m$^2$/g, pore volume=0.51 mL/g). In each case, a solution containing the rhodium precursor was first impregnated onto the support using an incipient wetness technique and then a solution containing the indium precursor was used to impregnate the support using the same incipient wetness technique as outlined below.

When nitrate precursor salts were employed, the rhodium component was obtained by diluting rhodium nitrate (Strem chemicals, 10.01 wt % solution) with deionized water to 3.51 wt % rhodium, whereas the indium component was obtained by dissolving solid indium nitrate trihydrate (Prochem) in sufficient deionized water to give a solution containing 110.0 wt % indium. When a rhodium oxoacetate precursor was used, this was prepared by adding hexa (acetato)-µ-oxotris(aqua)trirhodium(III) acetate (Alfa, 0.88 g) added to 2.08 g glacial acetic acid and 1.32 g deionized water, whereafter the resultant mixture was shaken until all solid dissolved and then diluted with a further 9.54 g deionized water to afford a 2.47 wt % Rh solution. When a rhodium acetylacetate precursor was used, this was prepared by dissolving rhodium (2,4-pentanedionate), i.e., rhodium (acetylacetonate), (Aldrich) in a mixture of methanol and 2,4-pentanedione such that the concentrations were 1.62 wt % rhodium and 23.0 wt % 2,4-pentanedione. An indium formate precursor was synthesized by refluxing indium hydroxide (Alfa, 3.20 g) with 60.72 g formic acid (Aldrich) in a round bottom flask with stirring overnight to obtain a homogeneous, colorless solution. The solvent was then evaporated by bailing the solution to leave an off-white solid, whereafter the resultant solid indium formate was dissolved in a mixture of formic acid and water such that the indium concentration was 2.1 wt % and the concentration of formic acid was about 60%.

Details of the catalyst preparations are set out below.

In Example 23, the prepared rhodium nitrate solution (226.8 μL) was mixed with deionized water (523.2 μL) and the diluted rhodium nitrate solution (125 μL) was added to 230 mg of ceria-alumina and agitated by vibration for 30 minutes at room temperature. The obtained material was dried at 120° C. for 3 hours and then calcined in air at 450° C. for 4 hours. Following calcination, the obtained agglomerated solid was gently broken up with a spatula. The prepared indium nitrate solution (117.6 μL) was mixed with deionized water (632.4 μL). This diluted indium nitrate solution (125 μL) was added to the calcined product of the first impregnation and agitated by vibration for 30 minutes at room temperature. The obtained material was dried at 120° C. for 3 hours and then calcined in air at 450° C. for 4 hours. The calcined catalyst was then subjected to reduction in a stream of 5% $H_2$ in $N_2$ at 450° C. for 5 hours.

In Example 24, the prepared indium formate solution (716.9 μL) was mixed with deionized water (33.1 μL) and the diluted indium formate solution (125 μL) was added to the calcined product of the first impregnation of Example 23 and agitated by vibration for 30 minutes at room temperature. The obtained material was dried at 120° C. for 3 hours and then calcined in air at 450° C. for 4 hours. The calcined catalyst was then subjected to reduction in a stream of 5% $H_2$ in $N_2$ at 450° C. for 5 hours.

In Example 25, the prepared rhodium(oxo)acetate solution (322.3 μL) was mixed with deionized water (427.7 μL). This diluted rhodium(oxo)acetate solution (125 μL) was added to 230 mg of ceria-alumina and agitated by vibration for 30 minutes at room temperature. The obtained material was dried at 120° C. for 3 hours and then calcined in air at 450° C. for 4 hours. Following calcination, the obtained agglomerated solid was gently broken up with a spatula. The prepared indium nitrate solution (117.6 μL) was mixed with deionized water (632.4 μL). This diluted indium solution (125 μL) was added to the calcined product of the first impregnation and agitated by vibration for 30 minutes at room temperature. The obtained material was dried at 120° C. for 3 hours and then calcined in air at 450° C. for 4 hours. The calcined catalyst was then subjected to reduction in a stream of 5% $H_2$ in $N_2$ at 450° C. for 5 hours.

In Example 26, the prepared indium formate solution (716.9 μL) was mixed with deionized water (33.1 μL) and the diluted indium formate solution (125 μL) was added to the calcined product of the first impregnation of Example 25 and agitated by vibration for 30 minutes at room temperature. The obtained material was dried at 120° C. for 3 hours and then calcined in air at 450° C. for 4 hours. The calcined catalyst was then subjected to reduction in a stream of 5% $H_2$ in $N_2$ at 450° C. for 5 hours.

In Example 27, methanol (25 μL),was added to 230 mg of ceria-alumina to allow for particle wetting. The prepared rhodium(acetylacetonate) solution was warmed above 50° C. until it became homogeneous and then 85.2 μL was added to the prepared ceria-alumina and agitated by vibration.

Another 50 μL of methanol was added to the sample and vibration was continued for 30 minutes. The obtained material was dried at 120° C. for 3 hours and then calcined in air at 450° C. for 4 hours. Following calcination, the obtained agglomerated solid was gently broken up with a spatula. The prepared indium nitrate solution (117.6 μL) was mixed with deionized water (632.4 μL). This diluted indium solution (125 μL) was added to the calcined product of the first impregnation and agitated by vibration for 30 minutes at room temperature. The obtained material was dried at 120° C. for 3 hours and then calcined in air at 450° C. for 4 hours. The calcined catalyst was then subjected to reduction in a stream of 5% $H_2$ in $N_2$ at 450° C. for 5 hours.

In Example 28, the prepared indium formate solution (716.9 μL) was mixed with deionized water (33.1 μL) and the diluted indium formate solution (125 μL) was added to the calcined product of the first impregnation of Example 27 and agitated by vibration for 30 minutes at room temperature. The obtained material was dried at 120° C. for 3 hours and then calcined in air at 450° C. for 4 hours. The calcined catalyst was then subjected to reduction in a stream of 5% $H_2$ in $N_2$ at 450° C. for 5 hours.

When the resultant catalysts were used to treat the same hydrocarbon feed under the same conditions as Example 1, the results shown in Table 5 were obtained.

TABLE 5

| Example | $C_2H_2$ conv (%) | $H_2$ conv (%) | $C_2H_4$ select (%) | $C_2H_6$ select (%) | Green Oil select (%) |
|---|---|---|---|---|---|
| 23 | 76.2 | 87.8 | 54.4 | 39.4 | 6.1 |
| 24 | 79.5 | 95.5 | 48.9 | 44.2 | 6.9 |
| 25 | 30.2 | 52.3 | −19.7 | 105.3 | 14.4 |
| 26 | 38.1 | 57.0 | 10.3 | 78.5 | 11.1 |
| 27 | 20.9 | 28.0 | 22.6 | 64.3 | 13.1 |
| 28 | 20.6 | 27.8 | 19.0 | 65.9 | 15.1 |

The results in Table 5 show that ceria-alumina is a useful support material and that nitrate appears to be the best precursor for rhodium and nitrates and formates are good precursors for indium.

EXAMPLES 29 TO 47

The sequential impregnation procedure and the rhodium and indium precursors of Examples 23 to 28 were used with the supports employed in Examples 6 to 16 to produce the following catalysts:

Example 29=0.6 wt % Rh (from nitrate)/1.2 wt % In (from formate) on $Al_2O_3$

Example 30=0.6 wt % Rh (from oxoacetate)/1.2 wt % In (from nitrate) on $Al_2O_3$ Example 31=0.6 wt % Rh (from oxoacetate)/1.2 wt % In (from formate) on $Al_2O_3$ Example 32=0.6 wt % Rh (from chloride)/1.2 wt % In (from nitrate) on $Al_2O_3$ Example 33=0.6 wt % Rh (from nitrate)/1.2 wt % In (from nitrate) on $SiO_2$ Example 34=0.6 wt % Rh (from nitrate)/1.2 wt % In (from formate) on $SiO_2$ Example 35=0.6 wt % Rh (from oxoacatetate)/1.2 wt % In (from nitrate) on $SiO_2$ Example 36=0.6 wt % Rh (from oxoacatetate)/1.2 wt % In (from formate) on $SiO_2$
Example 37=0.6 wt % Rh (from chloride)/1.2 wt % In (from formate) on $SiO_2$
Example 38=0.6 wt % Rh (from nitrate)/1.2 wt % In (from nitrate) on $ZrO_2$
Example 39=0.6 wt % Rh (from nitrate)/1.2 wt % In (from formate) on $ZrO_2$
Example 40=0.6 wt % Rh (from oxoacatetate)/1.2 wt % In (from nitrate) on $ZrO_2$
Example 41=0.6 wt % Rh (from oxoacatetate)/1.2 wt % In (from formate) on $ZrO_2$
Example 42=0.6 wt % Rh (from chloride)/1.2 wt % In (from formate) on $ZrO_2$
Example 43=0.6 wt % Rh (from nitrate)/1.2 wt % In (from nitrate) on $TiO_2$
Example 44=0.6 wt % Rh (from nitrate)/1.2 wt % In (from formate) on $TiO_2$
Example 45=0.6 wt % Rh (from oxoacatetate)/1.2 wt % In (from nitrate) on $TiO_2$
Example 46=0.6 wt % Rh (from oxoacatetate)/1.2 wt % In (from formate) on $TiO_2$
Example 47=0.6 wt % Rh (from chloride)/1.2 wt % In (from formate) on $TiO_2$ When the resultant catalysts were used to treat the same hydrocarbon feed under the same conditions as Example 1, the results shown in Table 6 were obtained.

TABLE 6

| Example | $C_2H_2$ conv (%) | $H_2$ conv (%) | $C_2H_4$ select (%) | $C_2H_6$ select (%) | Green Oil select (%) |
|---|---|---|---|---|---|
| 29 | 79.3 | 88.3 | 56.4 | 35.0 | 8.6 |
| 30 | 28.9 | 45.5 | 1.2 | 86.8 | 12.0 |
| 31 | 41.5 | 54.7 | 33.7 | 57.9 | 8.4 |
| 32 | 7.6 | 9.9 | 36.7 | 54.7 | 8.5 |
| 33 | 3.4 | 1.6 | 90.9 | 7.9 | 1.1 |
| 34 | 5.0 | 4.4 | 59.6 | 34.8 | 5.6 |
| 35 | 2.2 | 2.3 | 54.6 | 38.7 | 6.8 |
| 36 | 2.7 | 3.2 | 38.3 | 55.0 | 6.6 |
| 37 | 1.5 | 1.4 | 60.0 | 36.8 | 3.2 |
| 38 | 66.0 | 82.8 | 36.1 | 53.5 | 10.4 |
| 39 | 87.9 | 96.1 | 61.1 | 32.9 | 6.0 |
| 40 | 48.6 | 82.0 | −15.7 | 104.1 | 11.6 |
| 41 | 69.3 | 88.9 | 37.1 | 55.2 | 7.7 |
| 42 | 30.7 | 39.7 | 30.6 | 57.0 | 12.4 |
| 43 | 26.2 | 29.6 | 54.0 | 37.3 | 8.7 |
| 44 | 26.2 | 27.6 | 60.9 | 31.6 | 7.5 |
| 45 | 16.6 | 18.3 | 56.8 | 35.9 | 7.3 |
| 46 | 17.3 | 19.1 | 57.6 | 35.9 | 6.5 |
| 47 | 7.8 | 8.2 | 58.2 | 34.2 | 7.7 |

The results in Table 6 show that alumina and zirconia are superior support materials to silica and titania and that nitrate appears to be the best precursor for rhodium and nitrates and formates are good precursors for indium.

While the present invention has been described and illustrated by reference to particular embodiments, those of ordinary skill in the art will appreciate that the invention lends itself to variations not necessarily illustrated herein. For this reason, reference should be made solely to the appended claims for purposes of determining the true scope of the present invention.

The invention claimed is:

1. A catalyst composition effective for the selective hydrogenation of alkynes and diolefins to olefins including active components combined with a support, said active components consisting of:

(a) a rhodium component deposited from a nitrate precursor and present in an amount less than 3.0% of rhodium by weight of the total catalyst composition; and (b) an indium component deposited from a nitrate or formate precursor and present in an amount at least 0.3% and less than 5.0% of indium by weight of the total catalyst composition.

2. The catalyst composition of claim 1 and wherein rhodium is present in an amount at least 0.25% and less than 2.5% by weight of the total catalyst composition.

3. The catalyst composition of claim 1 and wherein rhodium is present in an amount at least 0.3% and less than 1.5% by weight of the total catalyst composition.

4. The catalyst composition of claim 1 and wherein indium is present in an amount at least 0.4% and less tan 4.0% by weight of the total catalyst composition.

5. The catalyst composition of claim 1 and wherein indium is present in an amount at least 0.4% and less than 3% by weight of the total catalyst composition.

6. The catalyst composition of claim 1 wherein the molar ratio of rhodium to indium is about 0.2 to about 1.1.

7. The catalyst composition of claim 1 wherein the molar ratio, of rhodium to indium is about 0.35 to about 0.75.

8. The catalyst composition of claim 1 and wherein said support is present.

9. The catalyst composition of claim 8 wherein the support is selected from alumina, zirconia and ceria-alumina.

10. The catalyst composition of claim 1 wherein the catalyst composition has been treated in a reducing atmosphere at a temperature of at least 300° C.

11. A method for making a catalyst composition, the method comprising:

(a) applying a rhodium nitrate to an alumina, zirconia, or ceria-alumina support; and (b) applying an indium formate or nitrate to the support; to produce a catalyst composition according to claim 1.

12. The method of claim 11 wherein the rhodium compound and the indium compound are applied to the support concurrently.

13. The method of claim 11 wherein the rhodium compound and the indium compound are applied to the support consecutively.

14. The method of claim 11 wherein at least one of the compounds is applied to the support by impregnating the support with a solution of the compound.

15. The method of claim 11 wherein at least one of the compounds is applied to the support by precipitating the compound from a solution containing ions of at least one of rhodium and indium.

16. The method of claim 11 and further including, after at least one of (a) and (b), calcining the support at a temperature of about 100° C. to about 600° C.

17. The method of claim 11 and further including, after (a) and (b), treating the support in a reducing atmosphere at a temperature of about 100° C. to about 600° C.

18. The method of claim 17 wherein said treating the support is conducted at a temperature of about 300° C. to about 500° C.

19. A supported catalyst composition consisting essentially of a rhodium component and an indium component said supported catalyst composition effective for the selective hydrogenation of alkynes and diolefins to olefins, wherein said support is selected from the group consisting of alumina, zirconia, or ceria-alumina; said catalyst composition further characterized as having less than 3.0% rhodium by weight of the total supported catalyst composition, deposited from rhodium nitrate; and having 0.3–5.0% indium by weight of the total supported catalyst composition, deposited from indium nitrate or indium formate.

20. The supported catalyst composition of claim 19, wherein said support is selected from the group consisting of theta alumina and zirconia.

* * * * *